United States Patent [19]

Yamaguchi et al.

[11] 4,188,339

[45] Feb. 12, 1980

[54] PROCESS FOR PREPARING ACRYLAMIDE AQUEOUS SOLUTION

[75] Inventors: Yasumasa Yamaguchi; Kazuo Kohno, both of Yokohama, Japan

[73] Assignee: Nitto Chemical Industry Co., Ltd., Tokyo, Japan

[21] Appl. No.: 843,472

[22] Filed: Oct. 19, 1977

[51] Int. Cl.$^2$ ............................................. C07C 103/08
[52] U.S. Cl. ................................. 260/561 N; 159/49
[58] Field of Search ............. 260/561 N; 159/49, 6 R, 159/4 CC

[56] References Cited

U.S. PATENT DOCUMENTS

| | | | |
|---|---|---|---|
| 2,890,155 | 6/1959 | Bueche | 159/49 X |
| 3,855,075 | 12/1974 | Nachtigall | 260/561 N X |
| 3,887,425 | 6/1975 | Munch | 260/561 N X |
| 3,900,516 | 8/1975 | Werges | 260/561 N |
| 3,917,693 | 11/1975 | Asano et al. | 260/561 N |
| 3,923,741 | 12/1975 | Asano et al. | 260/561 N |
| 3,941,837 | 3/1976 | Asano et al. | 260/561 N |
| 3,956,387 | 5/1976 | Dockner et al. | 260/561 N |

FOREIGN PATENT DOCUMENTS 233656  5/1969  U.S.S.R. ............................... 260/561 N

*Primary Examiner*—Arthur P. Demers
*Attorney, Agent, or Firm*—Sughure, Rothwell, Mion, Zinn and Macpeak

[57] ABSTRACT

A process for preparing an aqueous solution of acrylamide, which comprises catalytically hydrating acrylonitrile in the presence of a metal-containing catalyst to form a mixed aqueous solution containing about 15 to about 35% by weight of acrylamide and about 0.5 to about 20% by weight of acrylonitrile, and concentrating the mixed aqueous solution to a high concentration aqueous solution of acrylamide having an acrylonitrile concentration of about 0.1% by weight or less using a centrifugal film evaporator in which a stream of mixed aqueous solution and a stream of evaporated vapor flow countercurrently to each other.

11 Claims, 4 Drawing Figures

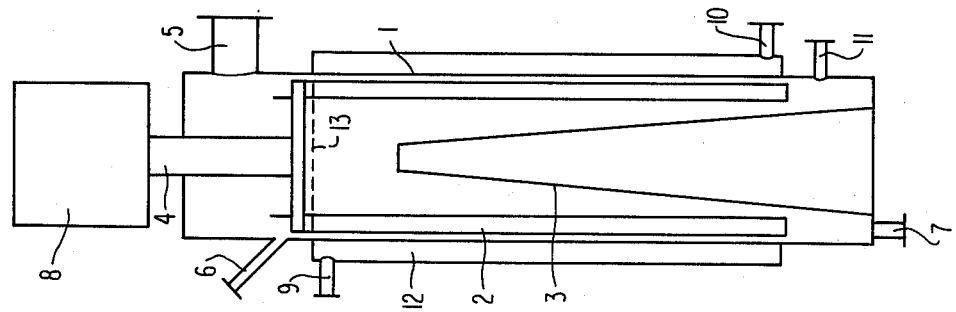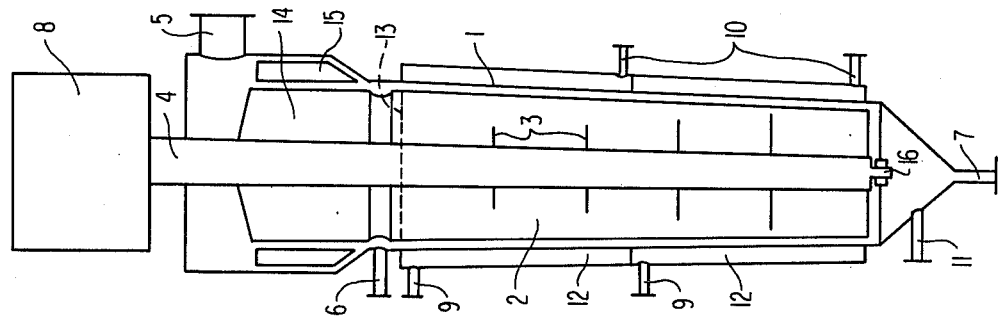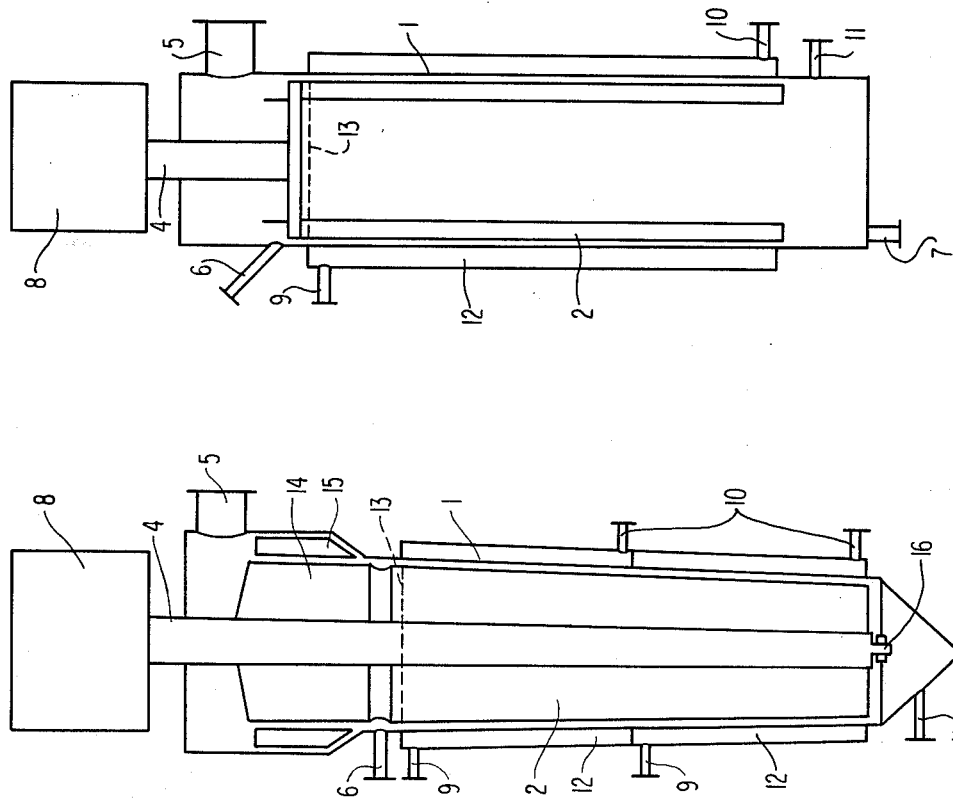

PROCESS FOR PREPARING ACRYLAMIDE AQUEOUS SOLUTION

BACKGROUND OF THE INVENTION

1. Field of the Invention

This invention relates to a process for preparing an aqueous solution of acrylamide. More specifically, the invention relates to an improvement in a process which comprises catalytically hydrating acrylonitrile in the presence of a metal-containing catalyst to form a solution of acrylamide, acrylonitrile and water, and increasing the concentration of acrylamide in the aqueous solution by removing the acrylonitrile and water.

2. Description of the Prior Art

Acrylamide is useful as a starting material for the production of polymers. For use as such a starting material, acrylamide must have the lowest possible acrylonitrile content, and the concentration of residual acrylonitrile should normally be less than about 0.1% by weight.

Previous practice e.g., as disclosed in U.S. Pat. Nos. 3,923,741 and 3,941,837, has been to use a distillation tower having a rectifying section and a heat evaporating section in order to obtain an aqueous solution of acrylamide from a mixed solution of acrylamide, acrylonitrile and water.

For heat evaporation, a stirred tank-type evaporation still, a forced circulation-type evaporation still or a horizontal cocurrent centrifugal evaporator has previously been used. When such a heat evaporator is used, it is difficult to reduce the concentration of acrylonitrile remaining in the solution to about 0.1% or less. It has been necessary, therefore, to reduce the acrylonitrile concentration by rectification.

A packed tower or a plate tower is used in the rectification section, and during rectification, the solution adheres to the inner wall of the rectifying tower, the inner wall of the packing, the undersurface of the trays, etc. Thus, these portions are not refreshed, and a polymerization of the adhering acrylamide may occur. The acrylamide polymer is water-soluble, and the inclusion of even a small amount of this polymer in the acrylamide aqueous solution decreases the quality. Furthermore, in order to prevent the polymerization of acrylamide during heat concentration, the concentrating operation must be performed at lower pressures and temperatures. Since a pressure drop occurs at the rectification section, the pressure at the condenser should be further reduced, making it difficult to condense the acrylonitrile.

SUMMARY OF THE INVENTION

An object of this invention, therefore, is to eliminate these defects of prior art techniques and to provide an aqueous solution of acrylamide having a concentration of as high as about 25 to 60% by weight and an extremely low content of acrylonitrile merely be continuously concentrating the acrylamide solution obtained by the catalytic hydration of acrylonitrile and containing a large amount of unreacted acrylonitrile without using a distillation tower.

Another object of this invention is to provide a high concentration aqueous solution of acrylamide with a very low concentration of an acrylamide polymer.

Still another object of this invention is to provide a process where the pressure in the condenser used for condensing vapor of acrylonitrile can be increased and where the condensation of acrylonitrile can be facilitated as a result of the ability to omit a rectifying section.

A further object of this invention is to reduce the conversion of acrylonitrile to acrylamide, ethylenecyanohydrin and ammonium acrylate, decrease the amounts of byproducts, and to achieve an acrylamide aqueous solution which is quite pure in a hydrating step.

In order to achieve these objects, extensive investigations of the recovery of acrylonitrile and the concentration of the aqueous solution of acrylamide have been made. The continuous concentration of a 31% by weight aqueous solution of acrylamide containing 2% by weight acrylonitrile to an acrylamide concentration of 36% by weight was attempted using each of a stirred tank-type evaporation still, a forced circulation-type evaporation still and a lateral cocurrent centrifugal film evaporator. It was found that the concentration of acrylonitrile remaining in the solution was 0.16 to 0.19% by weight, and it was impossible to reduce the concentration to about 0.1% by weight or less. Accordingly, when such evaporation stills are used, the acrylonitrile concentration must be reduced by rectification.

On the other hand, it was found that when a countercurrent centrifugal film evaporator in which a stream of the mixed solution and a stream of the evaporated vapor flow in opposite directions was used, the same aqueous solution as described above was concentrated to the acrylamide aqueous solution of the same concentration as described above, the concentration of acrylonitrile remaining in the solution could be reduced to 0.030% by weight, thus obviating the need for rectification, and a high concentration aqueous solution of acrylamide having a very low acrylonitrile content could be obtained.

It was also found that a solution containing 15 to 35% by weight of acrylamide and 0.5 to 20% of acrylonitrile, obtained by catalytically hydrating acrylonitrile in the presence of a metal-containing catalyst while adjusting the ratio between acrylonitrile and water and the conversion of acrylonitrile, was suitable as a starting material for this concentration because it has a low content of by-product impurities and is very advantageous for commercial production.

Accordingly the present invention provides a process for preparing an aqueous solution of acrylamide, which comprises catalytically hydrating acrylonitrile in the presence of a metal-containing catalyst to form a mixed aqueous solution containing about 15 to about 35% by weight of acrylamide and about 0.5 to about 20% by weight of acrylonitrile, and concentrating the aqueous solution to a high concentration aqueous solution of acrylamide having an acrylonitrile concentration of about 0.1% by weight or less using a centrifugal film evaporator in which a stream of the mixed aqueous solution and a stream of the vapor flow countercurrently to each other.

BRIEF DESCRIPTION OF THE ACCOMPANYING DRAWINGS

FIGS. 1 and 2 are sectional views showing generally employed countercurrent centrifugal film evaporators which do not contain any restrictive members, FIG. 3 is a sectional view showing a countercurrent centrifugal film evaporator including restricting members fitted to a stirrer, and FIG. 4 is a sectional view of a countercurrent centrifugal film evaporator including a restricting member of a truncated cone shape.

DETAILED DESCRIPTION OF THE INVENTION

Catalytic hydration of acrylonitrile, which is described in detail in, e.g., U.S. Pat. Nos. 3,597,481, 3,794,682 and 3,941,837 and Japanese Patent Application (OPI) No. 13,314/75, can be performed in a suspended bed or in a fixed bed. A suitable weight ratio of acrylonitrile to water in the starting material is about 1:9 to about 1:1 because low starting concentrations of acrylonitrile cause the aqueous acrylamide solution to be dilute and this is disadvantageous for concentration, and if the starting concentration of acrylonitrile is too high, the rate of the reaction decreases.

The conversion of acrylonitrile increases if the residence time in the reaction apparatus is prolonged. However, since with longer residence times, the amount of by-product ammonium acrylate increases, the conversion of acrylonitrile is preferably about 20 to about 95%, and up to 98% at the highest. The mixed solution obtained under these preferred conditions contains about 15 to about 35% of acrylamide and about 0.5 to about 20% of acrylonitrile.

Examples of the metallic component of the metal-containing catalyst used in the hydration of the acrylonitrile are metals such as Cu, Ag, Zn, Cr, Mn, Fe, Co, Ni, Ru, Rh, Pd and Pt, and the oxides and the salts of these metals. Coper-containing catalysts, especially metallic copper, are preferred. These metals can be used individually or as a mixture thereof. The metal-containing catalyst may be used either unsupported or supported on a carrier e.g., such as activated carbon, carbon black, graphite, alumina, silica gel, etc.

The hydration reaction is carried out at room temperature (about 20°–30° C.) to about 300° C., especially 60° to 150° C. The residence time is adjusted such that the conversion of acrylonitrile becomes about 20 to about 98%, preferably 40 to 90%. The solution so obtained is a mixed aqueous solution containing about 15 to about 35% of acrylamide and about 0.5 to about 20% of acrylonitrile and is substantially free from impurities ascribable to side-reactions.

The mixed aqueous solution, either as such or after having been concentrated by flash evaporation (e.g., as disclosed in Japanese Patent Application (OPI) No. 36,616/74), is introduced into a countercurrent centrifugal film evaporator. The term countercurrent centrifugal film evaporator as used herein generically denotes a centrifugal film evaporator of the type in which a stream of a mixed aqueous solution and a stream of an evaporated vapor thereof flow countercurrently to each other. Where flash evaporation is used the mixed aqueous solution is introduced into the flash evaporator at a temperature of about 60° to about 300° C., preferably 60° to 150° C. and removed as a more concentrated solution at a temperature of about 35° to about 70° C. The pressure generally employed in the flash evaporator is about 50 to about 760 mmHg.

Examples of a centrifugal film type of evaporator are shown in FIGS. 1, 2, 3 and 4 of the accompanying drawings.

The evaporator which contains restrictive members as shown in FIGS. 3 and 4 is more effective to achieve the object of the present invention as compared with the evaporator as shown in FIGS. 1 and 2 (which does not contain any restrictive members). Therefore, the present invention will be explained with reference to FIGS. 3 and 4.

Referring to FIG. 3, the mixed aqueous solution is passed in an inlet 6, and descends in a film form along a heat transmission surface 1. The heat transmission surface 1 is heated by steam which is passed into a jacket 12 through a vapor inlet 9 and which leaves from a drain outlet 10. The heat transmission surface 1 thus heats the liquid film of the mixed aqueous solution to generate a vapor containing acrylonitrile. Within the evaporator, a shaft 4 having a stirring vane 2 driven by a drive means 8 is rotated, e.g., at a peripheral speed of about 2 to 20 m/sec. The restricting members 3 are secured to the shaft 4. In FIG. 3, the restricting members 3 are so constructed that their size is larger the lower they are positioned to prevent a back-flow of the vapor. On descending, the solution of acrylamide is concentrated, and removed from a concentrate outlet 7. Generally, a suitable residence time is about 10 sec. to about 5 min. and a suitable inlet flow rate for the mixed aqueous solution into the evaporator is about 0.01 to 5 m/sec. and a suitable outlet flow rate for the concentrated solution of acrylamide from the evaporator is about 0.001 to 5 m/sec. Steam at about 55° to 180° C. can be used in the jacket 12. The water vapor and acrylonitrile evaporated rise, and are removed from a vapor outlet 5 after mist is separated by a mist separator 14 and a mist separator buffer 15. The evaporator is maintained at a pressure of about 20 to about 760 mmHg, preferably 50 to 140 mmHg, and if desired, an inert gas such as nitrogen, or steam may be fed from an inert gas inlet 11 to promote evaporation of the acrylonitrile. In FIG. 3, reference numeral 13 represents a vapor outlet from the heat evaporation zone, and 16, a bottom bearing of the stirrer.

In FIG. 4, the restricting member 3 has the shape of a truncated cone. When the mixed aqueous solution containing acrylamide and acrylonitrile is fed into the evaporator, the amount of the vapor evaporated by heating becomes a maximum at the vapor outlet 5, and becomes a minimum at the condensate outlet 7. Hence, the solution which flows down along the heat transmission surface 1 near the outlet 7 has a reduced opportunity to contact the vapor, and the evaporated acrylonitrile very seldom is re-dissolved. Thus, a high concentration aqueous solution of acrylamide having an acrylonitrile content of about 0.1% by weight or less can be obtained.

In contrast, in an evaporator in which a stream of the mixed aqueous solution fed and a stream of the vapor flow cocurrently, the acrylonitrile content increases, and cannot be reduced to about 0.16% by weight or less. In order to reduce the acrylonitrile content to about 0.1% by weight or less, it is necessary to rectify the aqueous solution of acrylamide.

The acrylonitrile content can be reduced in this invention using the counter current centrifugal film evaporate but can be further reduced in this invention is restricting members are provided for the prevention of the back-flow of the vapor in the countercurrent centrifugal film evaporator. The restricting members may have various shapes, for example, partition plates fitted to the stirring shaft or stirring vane, or a truncated cone shape. Desirably, the restricting members are provided at two or more, preferably 3 to 10, positions within the heat evaporating zone, and the cross-sectional area of the flow passage at the positions where the restricting members are located is about 0.01 to about 0.9 of the cross-sectional area of the flow passage of the vapor outlet of the heat evaporation zone at which the amount of the stream of vapor becomes a maximum. Furthermore, since in the latter half of the heat evaporation zone, the amount of the vapor becomes less than about one half of the total amount of the evaporated vapor, use of two or more portions whose cross-sectional area of flow passage is about 0.01 to about 0.5 of the flow passage cross-sectional area at the vapor outlet is preferred.

If concentration is carried out twice using two countercurrent centrifugal film evaporators arranged in series, the concentration of acrylonitrile can be even further reduced, e.g., to about 0.0012% by weight or less. The countercurrent centrifugal film evaporator may be a vertical or a transverse type.

If desired, a polymerization inhibitor may be added, e.g., in an amount of about $10^{-6}$ to $2 \times 10^{-3}$ parts by weight per part by weight of acrylamide. A suitable polymerization inhibitor is nitrogen oxide.

The process of this invention can be used to produce a high concentration aqueous solution of acrylamide having an acrylamide concentration of about 25 to about 60% by weight and an acrylonitrile content of about 0.1% by weight or less using only a countercurrent centrifugal film evaporator without using a distillation tower. Since a distillation tower is not required, the equipment cost is reduced, and polymerization difficulties in the distillation tower are eliminated. Hence, operation is easy, and no acrylamide polymer is dissolved in the concentrated aqueous solution of acrylamide. Furthermore, since a pressure drop does not occur at the rectifying column, the pressures of water vapor and acrylonitrile in the condenser can be increased, and the water vapor and acrylonitrile can be easily condensed. The loss of acrylonitrile is also reduced.

Furthermore, since the recovery of unreacted acrylonitrile is easy, the conversion of acrylonitrile in the catalytic hydration step can be decreased. The rate of reaction can therefore be increased, and the presence of by-products caused by side reactions can be prevented. Thus, an aqueous solution of acrylamide having a high purity can be obtained. These are the superior advantages of the invention which cannot be achieved using prior art techniques.

The following examples are given to illustrate the present invention in greater detail. Unless otherwise indicated, all parts, percents, ratios and the like are by weight.

EXAMPLE 1

Acrylonitrile and pure water which had been deoxygenated by distillation were introduced into a stirring tank at a flow rate of 30 parts/hr and 70 parts/hr, respectively. The stirring tank included a liquid withdrawal outlet equipped with a filter. A copper catalyst (30 parts) was fed into the tank, and the temperature of the inside of the tank was maintained at 100° C. The hydration of acrylonitrile was performed while the average residence time of the solution in the tank was maintained at 3 hours. The reaction solution was continuously withdrawn from the liquid withdrawal outlet equipped with the filter.

The reaction solution contained 24% of acrylamide and 12% of unreacted acrylonitrile. The solution was sent to a vessel at a pressure of 100 mmHg, and flash-evaporated to obtain 77 parts/hr of a solution containing 31% of acrylamide and 2% of acrylonitrile.

The solution was continuously concentrated using a vertical type countercurrent centrifugal film evaporator (which did not include a restricting member) of the type shown in FIG. 1 by external heating using steam at a temperature of about 100° to about 120° C. under a pressure of 80 mmHg. The solution was fed from the concentrate outlet 6 and, due to the centrifugal force provided by the stirring vane 2, was formed into a liquid film which flowed down. The concentrate, which was heated by steam from the outside of the heat transmission surface 1 and concentrated, was discharged from the concentrate outlet 7. Thus, a solution containing 36% of acrylamide and 0.030% of acrylonitrile was obtained at a flow rate of 67 parts/hr. and at a temperature of about 45° C.

The resulting aqueous solution was treated with an ion exchange resin to remove impurities, and could be used for polymerization. Acrylonitrile and water vapor flowed in an upward direction and were removed from the vapor outlet 5 via the mist separator 14. The acrylonitrile and water which distilled out could be reused as raw materials for the hydration reaction.

EXAMPLE 2

An acrylamide aqueous solution which had been obtained by hydration and flash evaporation in the same manner as in Example 1 was concentrated continuously using a vertical type countercurrent centrifugal film evaporator which did not contain a restricting member of the type shown in FIG. 1 at 80 mmHg, while passing nitrogen at a flow rate of 1 part/hr into the vicinity of an effluent withdrawal tube at the bottom of the evaporator. Thus, a solution containing 36% of acrylamide and 0.025% of acrylonitrile was obtained at a flow rate of 67 parts/hr.

EXAMPLE 3

An acrylamide aqueous solution obtained by hydration and flash evaporation in the same manner as in Example 1 was concentrated continuously at a pressure of 80 mmHg in two vertical countercurrent centrifugal film evaporators, neither of which contained a restricting member of the type described in FIG. 1, which were connected in series. The amount of heat was controlled to achieve almost the same concentration in the two evaporators as in Example 1. A solution containing 38% of acrylamide and 0.0012% of acrylonitrile was obtained at a flow rate of 63 parts/hr.

EXAMPLE 4

An acrylamide aqueous solution obtained by the same hydration as described in Example 1 was directly concentrated continuously at a pressure of 80 mmHg in a vertical type countercurrent centrifugal film separator (which did not contain a restricting member) of the type shown in FIG. 1. A solution containing 36% of acrylamide and 0.040% of acrylonitrile was obtained at a flow rate of 67 parts/hr.

EXAMPLE 5

An acrylamide aqueous solution obtained by the same hydration and flash evaporation as in Example 1 was continuously concentrated under a pressure of 80 mmHg in a vertical countercurrent centrifugal film evaporator including four circular restricting members fitted to the stirring vane of the type shown in FIG. 3.

A solution containing 36% of acrylamide and 0.0050% of acrylonitrile was obtained at a flow rate of 67 parts/hr.

When 10 cc of each of the acrylamide solutions obtained in Examples 1 to 5 was dissolved in 100 cc of methanol, no turbidity was observed, and an acrylamide polymer was not observed to be present.

EXAMPLE 6

An acrylamide aqueous solution obtained by the same hydration and flash evaporation as in Example 1 was continuously concentrated under a pressure of 80 mmHg in a vertical countercurrent centrifugal film evaporator which did not contain a restricting member of the type described in FIG. 1, while introducing 0.0077 part/hr of nitrogen oxide near an effluent withdrawal tube at the bottom of the evaporator.

When the apparatus was inspected after continuous operation for 3 days, no adhesion of polymer to the walls of the evaporator was observed.

While the invention has been described in detail and with reference to specific embodiments thereof, it will be apparent to one skilled in the art that various changes and modifications can be made therein without departing from the spirit and scope thereof.

What is claimed is:

1. A process for preparing an aqueous solution of acrylamide, which comprises
    catalytically hydrating acrylonitrile in the presence of a metal-containing catalyst to form a mixed aqueous solution containing about 15 to about 35% by weight of acrylamide and about 0.5 to about 20% by weight of acrylonitrile, then flash distilling the mixed aqueous solution obtained by hydration, and then
    concentrating the mixed aqueous solution obtained by flash distilling to a high concentration aqueous solution of acrylamide having an acrylonitrile concentration of about 0.1% by weight or less using a centrifugal film evaporator in which a stream of mixed aqueous solution and a stream of evaporated vapor flow countercurrently to each other and without using a distillation tower.

2. The process of claim 1, wherein the concentrating comprises concentrating the mixed aqueous solution using two of said centrifugal film evaporators connected in series.

3. The process of claim 1, wherein the process includes passing an inert gas or steam into the centrifugal film evaporator from a condensate outlet of the centrifugal film evaporator.

4. The process of claim 1, wherein the metal-containing catalyst is a copper-containing catalyst.

5. The process of claim 4, wherein the copper-containing catalyst is metallic copper.

6. A process for preparing an aqueous solution of acrylamide, which comprises catalytically hydrating acrylonitrile in the presence of a metal-containing catalyst to form a mixed aqueous solution containing about 15 to about 35% by weight of acrylamide and about 0.5 to about 20% by weight of acrylonitrile, then flash distilling the mixed aqueous solution obtained by hydration, and then concentrating the mixed aqueous solution obtained by flash distilling to a high concentration aqueous solution of acrylamide having an acrylonitrile concentration of about 0.1% by weight or less using a centrifugal film evaporator in which a stream of mixed aqueous solution and a stream of evaporated vapor flow countercurrently to each other and including a restricting member for preventing back-flow of the evaporated vapor to the heat evaporation zone, and without using a distillation tower.

7. The process of claim 6, wherein said centrifugal film evaporator contains two or more restricting members so that the cross-sectional area of the flow passage at the positions where the restricting members are located is about 0.01 to about 0.9 of the cross-sectional area of the flow passage at the vapor outlet of the heat evaporation zone at which the amount of the vapor flowing is maximum.

8. The process of claim 6, wherein the process includes passing an inert gas or steam into the centrifugal film evaporator from a condensate outlet of the centrifugal film evaporator.

9. The process of claim 2, wherein the process includes passing an inert gas or steam into the centrifugal film evaporator from a condensate outlet of the centrifugal film evaporator.

10. The process of claim 6, wherein the metal-containing catalyst is a copper-containing catalyst.

11. The process of claim 10, wherein the copper-containing catalyst is metallic copper.

* * * * *